(12) United States Patent
Kheim

(10) Patent No.: US 9,513,265 B2
(45) Date of Patent: Dec. 6, 2016

(54) PRESSURIZABLE INJECTION SEAT

(71) Applicant: AGILENT TECHNOLOGIES, INC., Loveland, CO (US)

(72) Inventor: Tobias Kheim, Waldbronn (DE)

(73) Assignee: Agilent Technologies, Inc., Santa Clara, CA (US)

(*) Notice: Subject to any disclaimer, the term of this patent is extended or adjusted under 35 U.S.C. 154(b) by 591 days.

(21) Appl. No.: 13/869,905

(22) Filed: Apr. 24, 2013

(65) Prior Publication Data

US 2013/0312499 A1 Nov. 28, 2013

(30) Foreign Application Priority Data

May 24, 2012 (GB) .................................. 1209147.6

(51) Int. Cl.
*G01N 30/22* (2006.01)
*G01N 30/16* (2006.01)
*G01N 30/18* (2006.01)

(52) U.S. Cl.
CPC .............. *G01N 30/22* (2013.01); *G01N 30/16* (2013.01); *G01N 2030/185* (2013.01); *Y10T 137/0379* (2015.04)

(58) Field of Classification Search
CPC ......................... G01N 30/16; G01N 2030/185
USPC .................... 73/61.55, 61.52, 61.56, 864.87
See application file for complete search history.

(56) References Cited

U.S. PATENT DOCUMENTS

| | | | | |
|---|---|---|---|---|
| 3,940,994 A * | 3/1976 | Klee | ...................... | G01N 30/22 73/864.81 |
| 3,999,439 A * | 12/1976 | Munk | ..................... | G01N 30/36 73/864.83 |
| 4,346,610 A * | 8/1982 | Ishii | ................... | G01N 35/1097 73/863.73 |
| 4,476,732 A * | 10/1984 | Yang | ...................... | G01N 30/20 73/863.73 |
| 6,526,812 B2 * | 3/2003 | Martin | ................... | G01N 30/18 422/70 |
| 7,101,477 B1 * | 9/2006 | Willis | .................... | B01D 15/20 210/198.2 |
| 2010/0230340 A1* | 9/2010 | Bielawski | .............. | F16J 15/166 210/198.2 |

FOREIGN PATENT DOCUMENTS

GB  1477581  6/1977
JP  2009274025  11/2009

OTHER PUBLICATIONS

GB Search Report dated Sep. 19, 2012 for Application No. GB1209147.6.

* cited by examiner

*Primary Examiner* — Michael A Lyons
*Assistant Examiner* — Suman K Nath

(57) ABSTRACT

An injection device comprising: a housing defining a space; a seat located in said space, the seat being configured for receiving a flow path element capable of injecting a pressurized fluid into the injection device through the seat; a pressure source for pressurizing a medium in said space, thereby reducing the pressure difference between the pressurized fluid in said flow path element and said medium.

20 Claims, 2 Drawing Sheets

PRESSURIZABLE INJECTION SEAT

CROSS-REFERENCE TO RELATED APPLICATIONS

The present application claims priority under 35 U.S.C. §119(a) and 35 U.S.C. §119(b) to GB Patent Application 1209147.6 filed on May 24, 2012. The entire disclosure of GB Patent Application 1209147.6 is specifically incorporated herein by reference.

BACKGROUND

A typical sample separation system for separating components of a sample fluid (particularly a sample liquid) comprises an injector for injecting the sample fluid into a mobile phase, and a fluid drive system for driving the mobile phase and the sample fluid through a separation unit, preferably a chromatographic column, which is adapted for separating components of the sample fluid in the mobile phase.

In high performance liquid chromatography (HPLC) the mobile phase is pressurized up to 1000 bar and above. In particular due to the high pressures it may occur that sample fluid leaks between an injection needle and a seat. Moreover, a carry-over of samples between subsequent injections may occur.

U.S. Pat. No. 6,526,812 B2 relates to a self-washing injection apparatus. The self-washing injection apparatus for liquid chromatography injection valves utilizes an interior chamber with a penetrable seal at a top end of the chamber and a needle sleeve seal at a bottom end of the interior chamber. A wash port in the body of the apparatus connects one or more sources of wash fluid to the interior chamber between the penetrable seal and a sleeve seal. The apparatus provides means to aspirate or pump wash fluids from one or more wash fluid reservoirs through the apparatus, the injection port of the injection valve and associated components. In particular, once the needle has been withdrawn from the apparatus, the injection port apparatus and the injection port of the injection valve may be washed or flushed utilizing the wash port.

SUMMARY

There may be a need for an improved technique that allows to reduce carry-over of samples between subsequent injections.

According to an exemplary embodiment of a first aspect of the herein disclosed subject-matter, an injection device is provided, the injection device comprising: a housing defining a space; a seat located in the space, the seat being configured for receiving a flow path element capable of injecting a pressurized fluid into the injection device through the seat; and a pressure source for a pressurizing medium in the space, thereby reducing the pressure difference between the pressurized fluid in the flow path element and the medium.

Embodiments of the herein disclosed subject-matter are based on the idea that pressurizing a medium in the space in which the seat is located reduces the pressure difference between the pressurized fluid in the flow path element on the one hand and the medium on the other hand. A lower pressure difference results in a lower amount of leakage. A lower amount of leakage in turn may reduce carry-over of samples between subsequent injections.

According to a representative embodiment, the pressure source comprises a pump device and a supply path, the pump device being configured for providing the medium under pressure through the supply path. Some leakage of the medium out of the space is acceptable in some embodiments. However, by providing conventional sealing techniques, for example high pressure sealing techniques, leakage of the medium out of the space is quite low. Accordingly in most embodiments a pump device with a relatively low pumping rate is sufficient. More important than the pumping rate is the pumping pressure achievable by the pump device. However, embodiments of the herein disclosed subject-matter are advantageous even if the pressure achieved in the space is for example only half of the pressure of the pressurized fluid in the flow path element. According to a representative embodiment, the pump device is a pump device similar to a pump device used for driving the mobile phase through a separation unit of a chromatography application.

According to a representative embodiment, the pressure source is configured so as to pressurize the medium to a pressure that is below the pressure of the pressurized fluid in the flow path element. According to a further embodiment, the pressure source is operated so as to pressurize the medium to a pressure that is below the pressure of the pressurized fluid in the flow path element.

According to a representative embodiment, the pressure source comprises a return path for flow of said medium out of the space. According to a representative embodiment, the supply path and the return path are provided by the same flow path. According to a further embodiment, the supply path and the return path are provided by different flow paths and hence the supply path is different from the return path. Providing the supply path different from the return path allows the cycling of the medium through the space. For example in a representative embodiment, the return path fluidly connects the space with the pressure source so as to cycle the medium through the supply path, the space and the return path. By providing a return path and cycling the medium through the space, a more precise pressure regulation may be achievable.

According to a representative embodiment, the housing comprises a base and a cover, wherein the seat is located in the base. For example, according to a representative embodiment the base and the seat may be configured according to known technology and embodiments of the herein disclosed subject-matter may be implemented by providing a cover according to embodiments of the herein disclosed subject-matter and pressurizing the space defined by the base and the cover according to embodiments of the herein disclosed subject-matter.

According to a representative embodiment, the cover is mounted or mountable on the base, wherein the cover and the base thereby define the space.

According to a representative embodiment, the cover is configured for being penetrable by the flow path element. For example, according to a representative embodiment the cover may comprise a housing body, wherein the housing body comprises a through hole facing the seat through which the flow path element can be inserted through the cover and into the seat. According to a representative embodiment, the housing body is a structural element providing structural rigidity to the cover.

According to a further embodiment, the through hole in the housing body is sealed with a pressure sealing, such as a high pressure sealing. In accordance with a representative embodiment, the pressure sealing is capable of withstanding pressures of up to 200 bar, optionally up to 500 bar, optionally up to 1200 bar or optionally up to even higher pressures. In accordance with a representative embodiment, the pressure seal covers the through-hole and is penetrable by the flow path element. For example, in a representative embodiment, the pressure seal comprises a membrane which is penetrable by the flow path element. However, any other pressure seal may be used, for example the penetrable seal disclosed by U.S. Pat. No. 6,526,812 B2, the disclosure of which is specifically incorporated herein by reference. According to a representative embodiment, the pressure seal is resilient or comprises a resilient element which is penetrable by the flow path element while upon removal of the flow path element the pressure seal seals the space defined by the housing due to its resilient property. However, it has to be pointed out that in accordance with a representative embodiment the space which is defined by the housing is pressurized only if the flow path element extends through the pressure seal. Hence, according to a representative embodiment the pressure seal may provide a sealing of the space only if the flow path element is inserted in the pressure seal and/or penetrates through the pressure seal. According to a representative embodiment, the pressure in the space may be relieved to ambient pressure before the flow path element is removed from the pressure seal.

According to other embodiments, the pressure seal is configured for sealing the space defined by the housing if the flow path element is removed from the pressure seal as well as if the flow path element penetrates through the pressure seal.

According to a representative embodiment, the term "pressurizing the space" includes "pressurizing the space by means of the medium" and "pressurizing the medium in the space". Further, according to a representative embodiment, the term "pressurizing the space" corresponds to "pressurizing the space at least up to a first pressure level". Furthermore, according to a representative embodiment, the term "pressurizing the medium" corresponds to "pressurizing the medium at least up to a first pressure level". The first pressure level may be above a pressure level employed for flushing the space, e.g. flushing the space with the medium. According to a representative embodiment, the method comprises flushing the space under a pressure below a first pressure level and pressurizing the medium in the space to a pressure above the first pressure level.

According to a representative embodiment, the medium is a fluid. For example, according to a representative embodiment the medium is a liquid. According to another embodiment, the medium is a gas. According to still another embodiment, the medium is a gel. According to a further embodiment, the medium comprises two or more medium components. For example, according to a representative embodiment the medium comprises a fluid. According to a further embodiment, the medium comprises a gel. According to a representative embodiment, the medium is selected to have a viscosity in a suitable viscosity range. The viscosity range suitable for a particular implementation of the injection device according to embodiments of the herein disclosed subject-matter may depend for example on the type and/or the particular implementation of the pressure sealing. For example, for simpler pressure sealings which comprise for example a membrane, a gel may provide suitable sealing properties of the membrane. Having the same membrane, a liquid with a very low viscosity may be unsuitable for pressurizing the medium due to insufficient sealing properties of the pressure sealing for low viscosity liquids. Hence, it should be understood that the selection of the medium may at least partially depend on the pressure seal. However, numerous variations of the pressure seal as well as in the viscosity of the medium are possible while still providing one or more advantages of the herein disclosed subject-matter.

According to a representative embodiment, the medium has a viscosity in at least one of the following ranges: between 0.0001 Pas and 300 Pas; between 0.0001 Pas and 0.01 Pas; between 0.01 Pas and 1.0 Pas; between 1.0 Pas and 200 Pas.

According to a further embodiment, the flow path element is an injection needle. Injection needles are typically used in chromatography applications. According to a representative embodiment, the injection device is an injection device of a measurement device. For example, in a representative embodiment, the measurement device is one of the following devices: a chromatography device; a column chromatography device; a liquid chromatography device; a high performance liquid chromatography device; a gas chromatography device; an electrical chromatography device, an electrophoresis device; a gel electrophoresis device; a microfluidic device and a nanofluidic device.

According to a further embodiment, the pressurized fluid which is injected through the seat is a liquid. An example of such a representative embodiment is a liquid chromatography application, wherein a sample fluid is injected into a mobile phase by means of the injection device. Hence, in such a representative embodiment the seat is fluidically coupled with a flow path for the mobile phase and an injection of the sample through the seat consequently leads to an injection of the sample into the mobile phase.

The pressure in the mobile phase might range from 2-200 MPa (20 to 2000 bar), in particular 10-150 MPa (100 to 1500 bar), and more particularly 50-120 MPa (500 to 1200 bar).

According to a further embodiment, the pressurized fluid is a gas.

According to a further embodiment, the injection device further comprises at least one of the following features: The pressure of the pressurized fluid is above 100 bar; the pressure of the pressurized fluid is above 300 bar; the pressure of the pressurized fluid is above 500 bar; the pressure of the pressurized fluid is above 1000 bar; the pressure of the pressurized fluid is above 1500 bar; the pressure of the pressurized fluid is above 2000 bar.

According to a further embodiment, the injection device further comprises a controller for controlling the pressure source. According to a representative embodiment, the controller is a processor device comprising at least one processor for executing a computer program to thereby provide the functionality of one or more embodiments of the herein disclosed subject-matter. According to a further embodiment, the controller is provided in hardware wherein the functionality of one or more embodiments of the herein disclosed subject-matter is implemented in discrete electronic circuits. Further, in another embodiment, the controller is a hybrid device wherein the functionality of one or more embodiments of the herein disclosed subject-matter is provided in software, whereas the functionality of one or more other embodiments of the herein disclosed subject-matter is provided in hardware.

According to a representative embodiment, the controller is configured so as to pressurize the medium if the flow path element is received in the seat. This can be achieved by any suitable configuration of the controller and the injection device.

According to a representative embodiment, the controller is configured for receiving a control signal indicating that a flow path element is received in the seat, wherein the controller, in response hereto, provides a control signal to the pressure source in order to pressurize the medium. Any such control signal indicating that the flow path element is received in the seat may be used to control the operation of the controller and the issuance of a control signal to the pressure source in order to pressurize the medium.

According to a representative embodiment, the injection device comprises a sensor providing a sensor signal which is indicative of the pressure in the medium, the controller controlling the pressure source in response to the sensor signal. According to a representative embodiment, the sensor for providing a sensor signal which is indicative of the pressure in the medium may directly measure the pressure of the medium. According to a further embodiment, the sensor is an indirect sensor sensing the pressure indirectly by measuring a quantity which depends on the pressure in the medium. For example, according to a representative embodiment the sensor may include a first component that moves or deforms under action of the pressure in the medium wherein the sensor comprises a second component for detecting the movement or deformation of the first component of the sensor.

According to a representative embodiment, the controller is configured for maintaining the pressure of the medium in the space in a predetermined range. For example, in a representative embodiment the controller is configured for controlling the pressure source in response to the sensor signal indicative of the pressure in the medium so as to maintain the pressure of the medium in the space in the predetermined range.

According to a representative embodiment, the injection device comprises a control element activatable by an operator in order to signal to the controller that the flow path element is received in the seat. For example, the control element which is activatable by an operator may be a user interface or a push button by which the operator directly signals to the controller that the flow path element is received in the seat. This requires recognition by the operator that the flow path element is received in the seat and appropriate action by the operator. Further, the control element may be a control element that is activated to provide the control signal indicating that a flow path element is received in the seat upon a respective change of an operating condition of the injection device or of an associated device, e.g. upon closing a cover or a shield of the injection device or of a measurement device which comprises the injection device.

According to a further embodiment, the injection device comprises a sensor for determining that the flow path element is received in the seat. Such a sensor may operate electrically, mechanically, optically, magnetically, etc.

According to a representative embodiment, the injection device comprises an actuator for coupling the flow path element and the seat, the controller determining from the operation of the actuator whether the flow path element is received in the seat. For example, according to a representative embodiment, the actuator is adapted for selectively fluidically coupling and fluidically uncoupling the flow path element and the seat. According to a representative embodiment, the controller receives a feedback signal from the actuator from which feedback signal the controller determines whether the flow path element is received in the seat. Hence, according to a representative embodiment, the actuator is configured for providing such a feedback signal to the controller. Further, according to a representative embodiment the controller is configured for controlling the actuator.

In such a representative embodiment the control signals, which are provided by the controller for controlling the actuator, are indicative of the position of the flow path element. For example, if the controller provides to the actuator the control signal to insert the flow path element into the seat, according to a representative embodiment the controller determines from an issuance of such a control signal that after a predetermined time after the issuance of the control signal, that the flow path element is received in the seat. Herein the predetermined time may be set to a suitable value ensuring that the flow path element is indeed received in the seat under operating conditions.

According to a further embodiment, the controller is configured for reducing the pressure of the medium in the space before the flow path element is removed from the seat. This may be advantageous for example in a representative embodiment where the pressure seal has a first sealing capability with the flow path element penetrating through the pressure seal whereas providing a second sealing capability that is lower than the first sealing capability if the flow path element is removed from the pressure seal. Hence, even in such a representative embodiment the respective configuration of the controller may reduce or prevent leakage of medium out of the pressure seal. In this regard, a higher sealing capability provides a higher maximum pressure the seal can withstand before it leaks.

According to a further embodiment, the controller is configured for providing a control signal to the pressure source, the control signal effecting the reduction of the pressure of the medium in the space. For example, in a representative embodiment where the pressure source comprises a pump, the control signal which effects reduction of the pressure of the medium in the space is configured to shut off the pump in a representative embodiment. According to a further embodiment, the controller is configured for operating a pressure relief valve in a return path to thereby open the return path to allow the medium to flow out of the space in order to effect reduction of the pressure of the medium in the space.

In this regard it is noted that the pressure source may be for example a pressure reservoir and a reducing valve for reducing the pressure in the pressure reservoir to a desired value corresponding to the desired pressure to which the medium in the space shall be pressurized.

According to a representative embodiment of a second aspect of the herein disclosed subject-matter, a measuring device for performing a measurement on a fluidic sample is provided, the measuring device comprising an injection device according to one or more embodiments of the herein disclosed subject-matter.

According to a further embodiment, the pressurized fluid is a sample fluid to be introduced into a mobile phase and the measuring device is a fluid separation system for separating compounds of the sample fluid in the mobile phase, wherein the injection device is provided for injection of the sample fluid into the mobile phase.

According to a representative embodiment, the measuring device comprises a mobile phase drive, preferably a pumping system, configured to drive the mobile phase through the fluid separation system. According to a further embodiment, the fluid separation system comprises a separation unit, preferably a chromatographic column, configured for separating compounds of the sample fluid in the mobile phase.

According to a representative embodiment of a third aspect of the herein disclosed subject-matter, a method of sealing a flow path connection site in an injection device is provided, wherein the flow path carries a pressurized fluid, the method comprising: pressurizing a medium which surrounds the flow path connection site to thereby reduce the pressure difference between the pressurized fluid in the flow path and the medium.

Reducing the pressure difference between the pressurized fluid in the flow path and the medium may reduce leakage and carry-over of samples between subsequent connection processes.

According to a representative embodiment, pressurizing a medium includes supplying the medium under pressure into a space which surrounds the flow path connection site. According to a representative embodiment, the flow path connection site comprises a seat and a flow path element received in the seat. According to a further embodiment, the medium is pressurized if the flow path element is received in the seat. According to a further embodiment, the medium is pressurized after the flow path element is received in the seat. According to a still further embodiment, the medium is only pressurized after the flow path element is received in the seat. According to a still further embodiment, the medium is pressurized only during a time period, wherein during the time period the flow path element is received in the seat.

According to a representative embodiment, the method comprises receiving a control signal indicating that the flow path element is received in the seat and, in response hereto, pressurizing the medium. According to a further embodiment, in response to the control signal indicating that the flow path element is received in the seat, the method comprises providing a control signal to the pressure source in order to pressurize the medium in response hereto.

According to a further embodiment, the method comprises maintaining the pressure of the medium in a predetermined range. According to a further embodiment, the method comprises maintaining the pressure of the medium in a predetermined range during pressurizing the medium.

According to a further embodiment, the method comprises receiving a sensor signal which is indicative of the pressure in the medium and controlling a pressure source in response to the sensor signal to thereby pressurize the medium. According to a representative embodiment, the pressure source is configured in accordance with one or more embodiments of the herein disclosed subject-matter.

According to a further embodiment, the method comprises receiving a control signal from a control element that is activatable by an operator, the control signal indicating that a flow path element is received in the seat and, in response hereto pressurizing the medium. The control element activatable by an operator may be configured in accordance with one or more embodiments of the herein disclosed subject-matter. For example, the control element may be a push button activatable by the operator or may be a switch that is activated in response to an operation the operator performs in order to conduct a measurement, for example closing a cover, etc.

According to a further embodiment, the method comprises receiving a sensor signal indicating that the flow path element is received in the seat and, in response hereto, pressurizing the medium. For example, the sensor signal indicating that the flow path element is received in the seat may be a sensor signal according to one or more embodiments of the herein disclosed subject-matter.

According to a further embodiment, the method comprises determining from the operation of an actuator that the flow path element is received in the seat, and, in response hereto pressurizing the medium. Determining from the operation of an actuator that the flow path element is received in the seat may be performed in accordance with one or more embodiments of the herein disclosed subject-matter. For example, the determination may be made from a driving signal provided to the actuator, from a feedback signal provided by the actuator, etc.

According to a further embodiment, the method comprises determining whether the flow path element is to be removed from the seat, and, in response hereto, reducing the pressure in the medium. According to a representative embodiment, the determination whether the flow path element is to be removed from the seat is made in accordance with one or more embodiments of the herein disclosed subject-matter. For example, according to a representative embodiment this determination can be made from a signal indicating that a measurement run has been completed. Further, according to a representative embodiment, the determination is made in response to a specific user action, e.g. pressing a button, opening a housing, etc. To implement such a method, respective hardware components such as switches, buttons, etc. may be provided. Further, additionally or alternatively for the hardware components, generally at least one user interface may be provided, the user interface allowing to make a determination whether the flow path element is to be removed from the seat.

According to a representative embodiment, removal of the flow path element from the seat is blocked until a freeing signal is received, the freeing signal indicating that the pressure in the medium is below a predetermined value. Determination as to whether the pressure in the medium is below the predetermined value can be made directly by measuring the pressure in the medium or indirectly by making a determination from at least one operating parameter, whether the pressure is or is likely below the predetermined value. The at least one operating parameter may include for example at least one of a control signal, a sensor signal, a feedback signal, etc.

According to a representative embodiment, the method comprises effecting reduction of the pressure of the medium by providing a control signal to a pressure source. The control signal may be provided automatically by a control unit or manually by a user interface operated by an operator.

According to a representative embodiment, the method further comprises effecting reduction of the pressure of the medium by opening a return path to allow the medium to flow away from the flow path connection site. For example, if the flow path connection site is located in a space filled with the medium, according to a representative embodiment, the reduction of the pressure of the medium is effected by opening the return path to allow the medium to flow out of the space.

According to a representative embodiment of a fourth aspect of the herein disclosed subject matter, a software program or product is provided, preferably stored on a data carrier, the software program or product being adapted for controlling or executing a method according to one or more embodiments of the herein disclosed subject matter, when run on a data processing system such as a computer.

As used herein, reference to a software program is intended to be equivalent to a reference to a program element and/or a non-transitory tangible computer readable medium containing instructions for controlling a computer system to effect and/or coordinate the performance of a method according to one or more embodiments of the herein disclosed subject matter.

The software program may be implemented as non-transitory tangible computer readable instruction code by use of any suitable programming language, such as, for example, JAVA, C++, and may be stored on a computer-readable medium (removable disk, volatile or non-volatile memory, embedded memory/processor, etc.). The instruction code is operable to program a computer or any other programmable device to carry out the intended functions. The computer program may be available from a network, such as the World Wide Web, from which it may be downloaded.

Various representative embodiments may be realized by means of a software program respectively software. However, the various representative embodiments may also be realized by means of one or more specific electronic circuits respectively hardware. Furthermore, the various embodiments may also be realized in a hybrid form, i.e. in a combination of software modules and hardware modules. Software programs or routines can be preferably applied in or by the control unit.

In the above there have been described and in the following there will be described exemplary embodiments of the subject matter disclosed herein with reference to an injection device and a respective method. It has to be pointed out that of course any combination of features relating to different aspects of the herein disclosed subject matter is also possible. In particular, some embodiments have been or will be described with reference to apparatus type features whereas other embodiments have been or will be described with reference to method type features. However, a person skilled in the art will gather from the above and the following description that, unless otherwise notified, in addition to any combination of features belonging to one aspect also any combination between features relating to different aspects or embodiments, for example even between features of the apparatus type embodiments and features of the method type embodiments is considered to be disclosed with this application.

According to embodiments of the herein disclosed subject matter, apparatus type features are adapted for providing the functionality of one or more of the embodiments of the method type features and/or for providing the functionality as required by one or more of the method type features.

According to further embodiments of the herein disclosed subject matter, method type features are adapted for providing the functionality of one or more of the embodiments of the apparatus type features and/or for providing the functionality as required by one or more of the apparatus type features.

BRIEF DESCRIPTION OF DRAWINGS

Other objects and many of the attendant advantages of embodiments of the present teachings will be readily appreciated and become better understood by reference to the following more detailed description of embodiments in connection with the accompanying drawings. Features that are substantially or functionally equal or similar will be referred to by the same reference signs.

Figure 1:
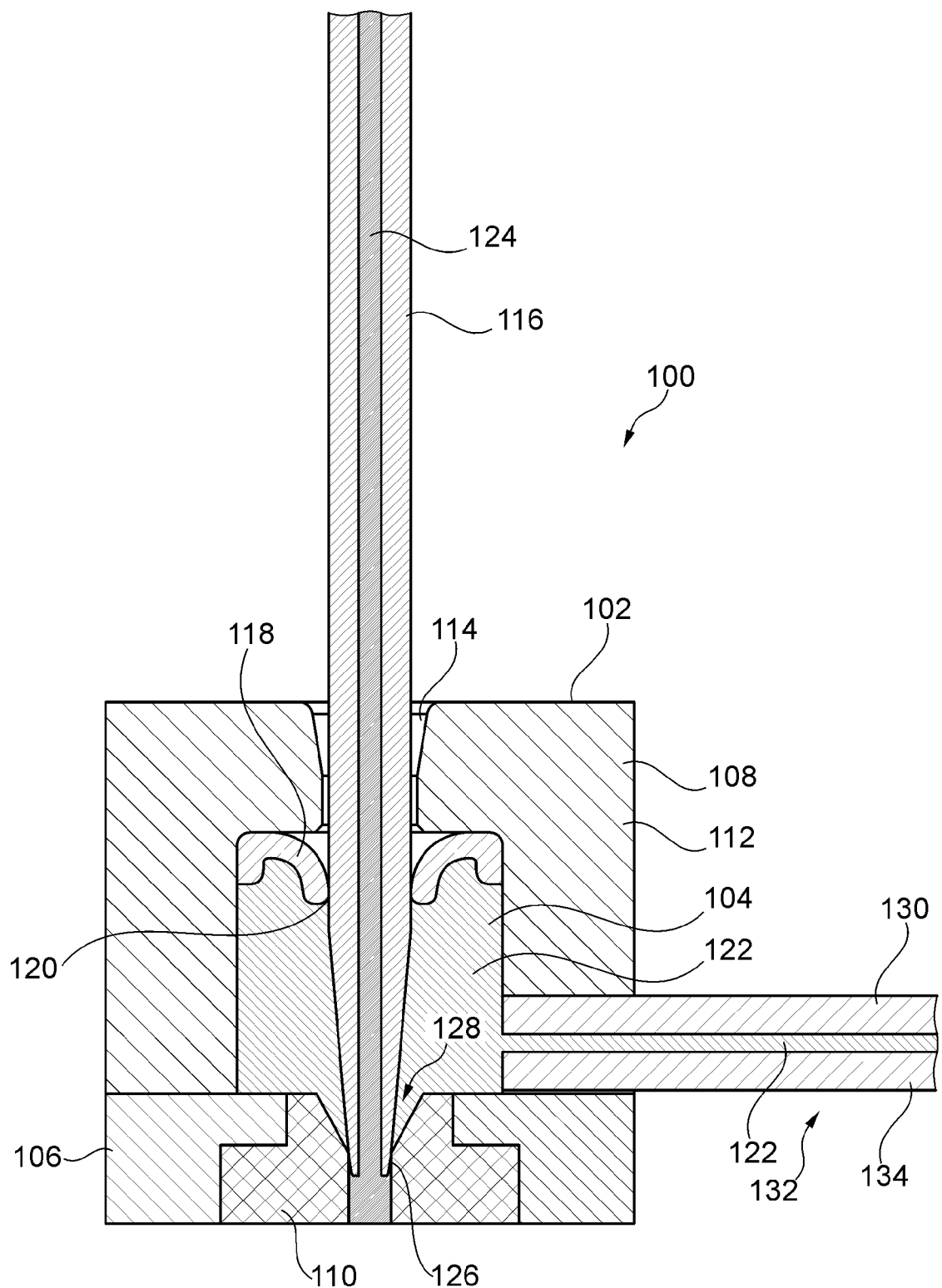
FIG. 1 shows an injection device in accordance with embodiments of the herein disclosed subject-matter.

The illustration in the drawings is schematic.

DETAILED DESCRIPTION

Generally, the present teachings relate to injection devices, measuring devices and a method of sealing a flow path connection site in an injection device. The present teachings further relate to a sample separation system, in particular a high performance liquid chromatography application. In a representative embodiment, pressurizing a flow path connection site in an injection device is provided to reduce leakage or carry-over between subsequent connections performed at the flow path connection site.

In the following, reference is made to an injection device of a high performance liquid chromatography application. However, it should be understood that reference to such an injection device is merely exemplary and that embodiments of the herein disclosed subject-matter may be applied to any other injection device as well.

FIG. 1 shows an injection device 100 in accordance with embodiments of the herein disclosed subject-matter.

The injection device 100 comprises a housing 102 defining a space 104. In accordance with a representative embodiment, the housing 102 comprises a base 106 and a cover 108. The base 106 comprises a seat 110, the seat being located in the space 104. In accordance with a representative embodiment, the seat 110 is provided in the base 106.

In accordance with a representative embodiment, the cover 108 comprises a housing body 112 which according to a representative embodiment is a structural element of the cover 108. For example, in accordance with a representative embodiment, the housing body 112 bears most of the forces being exerted on the cover 108 by pressurizing the space 104. According to a representative embodiment, the housing body 112 comprises a through-hole 114 opposite the seat 110. The through-hole 114 allows a flow path element 116, such as an injection needle, to be inserted into the housing 102 in order to be received by the seat 110.

In accordance with a representative embodiment, the through-hole 114 is sealed by a pressure seal 118 which is penetrable by the flow path element 116.

In accordance with a representative embodiment, the pressure seal 118 is provided in the form of a membrane, e.g. as shown in FIG. 1. In accordance with a representative embodiment, the membrane comprises a through-hole 120 through which the flow path element 116 can penetrate. In accordance with a representative embodiment, the dimension of the through-hole is such that the through-hole is closed by resilient expansion and/or bending of the pressure seal 118 if the flow path element 116 is removed from the membrane. Hence, in such a representative embodiment the pressure seal 118 seals the space 104 even if no flow path element 116 is present in the pressure seal 118, at least up to a certain predetermined first pressure.

According to a representative embodiment, the space 104 is filled with a medium 122. It should be understood that the predetermined first pressure depends on the configuration of the pressure seal 118 as well as on the physical properties of the medium 122, e.g. the surface tension of the medium 122, the viscosity of the medium 122, etc.

In accordance with a representative embodiment, the flow path element 116 is provided for injecting a pressurized fluid 124 into the injection device 100 through the seat 110. It should be understood that the seat 110 is fluidically coupled to a cavity or flow path of the injection device 100 which is not shown in FIG. 1. According to a representative embodiment, the flow path element 116 is sealingly received in the seat 110. In other words, the sealing connection between the flow path element 116 and the seat 110, which sealing connection is indicated at 126 in FIG. 1, is tight for the pressurized fluid 124 in the flow path element 116 at least up to a predetermined second pressure. However, the sealing connection 126 between the flow path element 116 and the seat 110 may be established with different flow path elements 116. In particular, at least in some applications different flow path elements 116 are used with the same seat 110. Hence, in such a case manufacturing tolerances etc. may lead to different predetermined second pressures up to which the sealing connection 126 is tight for the pressurized medium. Therefore, it would be advantageous to provide a tight sealing connection 126 even if manufacturing tolerances of the flow path element 116 occur.

According to a representative embodiment, the medium 122 in the space 104 is pressurized, thereby reducing the pressure difference between the pressurized fluid 124 in the flow path element 116 and the medium 122. The tightness of the sealing connection 126 may depend indeed on the pressure difference between the pressurized fluid 124 in the flow path element 116 and the medium 122 in the space 104 surrounding a flow path connection site 128, e.g. the connection site between the seat 110 and the flow path element 116. In such a case the reliability of the sealing connection 126 can be increased by reducing the pressure difference between the pressurized fluid 124 in the flow path element 116 and at a medium 122.

According to a representative embodiment, a supply path 130 for the medium 122 is provided, the supply path 130 being part of a pressure source 132 which is provided for pressurizing the medium 122 in the space. In accordance with a representative embodiment, the medium 122 in the space 104 is pressurized by supplying the medium 122 under pressure through the supply path 130. According to a representative embodiment, the injection device 100 comprises a return path 134 for providing for flow of the medium 122 out of the space 104 if desired. In accordance with a representative embodiment, the return path 134 and the supply path 130 are provided by the same flow path, as shown in FIG. 1. According to other embodiments, the supply path 130 and the return path 134 are provided by different flow paths.

Figure 2:
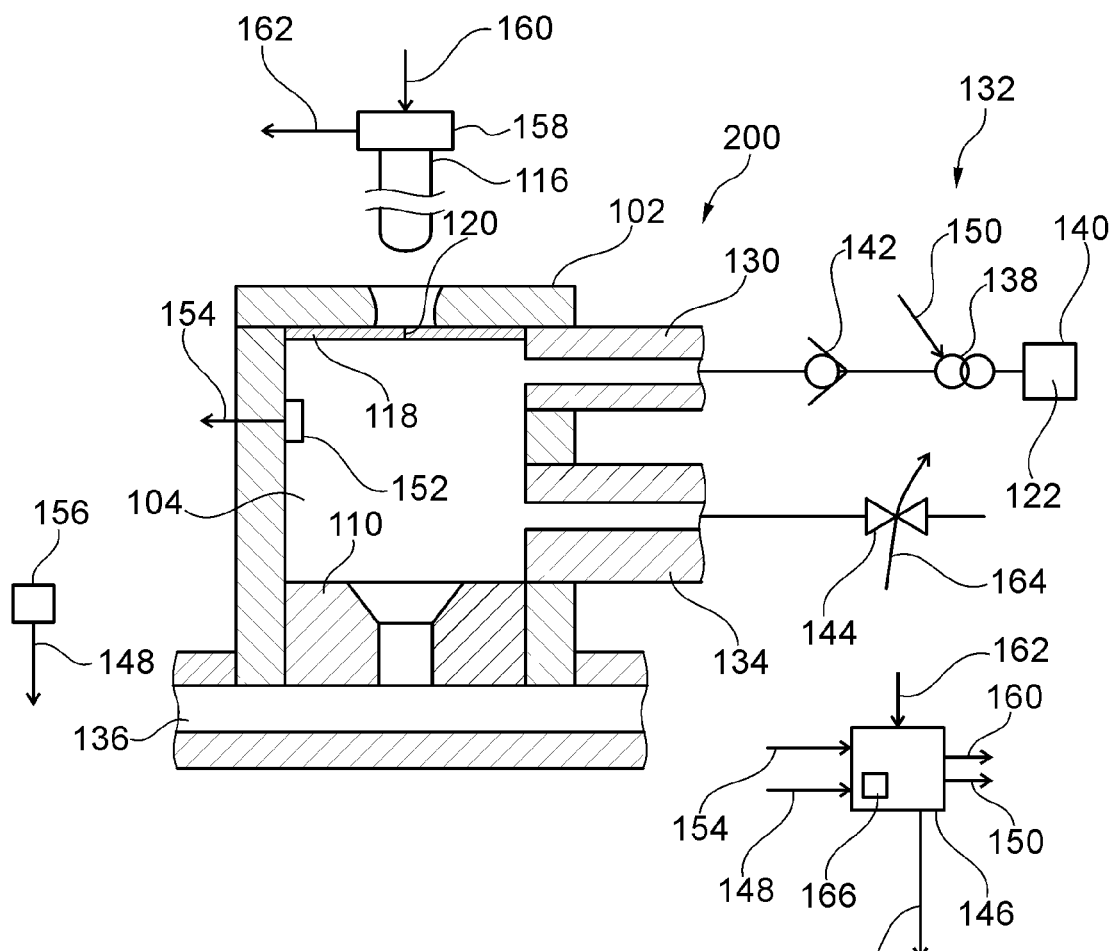
FIG. 2 shows an injection device in accordance with embodiments of the herein disclosed subject-matter.

FIG. 2 shows an injection device 200 in accordance with embodiments of the herein disclosed subject-matter.

The injection device 200 is configured similar to the injection device 100 of FIG. 1. Hence, similar elements are provided with the same reference signs and the description of these elements is not repeated here. Rather the differences between the injection device 100 in FIG. 1 and the injection device 200 of FIG. 2 are described.

FIG. 2 shows the injection device 200 without the flow path element 116 inserted into the seat 110. Hence the pressure seal 118, which in accordance with a representative embodiment has resilient properties, is bent and expanded in order to close a through-hole 120 in the membrane at least up to the predetermined first pressure. Further, in accordance with a representative embodiment, the injection device 200 comprises a flow path 136 which is in fluid communication with the seat 110, thereby making it possible to inject a pressurized fluid through the flow path element 116 and through the seat 110 into the flow path 136.

In accordance with a representative embodiment, the supply path 130 and the return path 134 of the injection device 200 are provided as different individual flow paths. In accordance with a representative embodiment, the supply path 130 comprises a pump device 138 for pumping the medium 122 from a reservoir 140 into the space 104. In accordance with a representative embodiment, the supply path 130 may optionally include a check valve 142 such that a pressure of the medium 122 in the space 104 may be maintained even if the pump device 138 is shut off. In other embodiments, the supply path 130 does not include the check valve 142. According to a representative embodiment, the return path 134 comprises a pressure relief valve 144 for selectively opening and closing the return path 134. In accordance with a representative embodiment, the return path 134 may be fluidically connected to the reservoir 140 or may be fluidically connected to a waste. It should be understood that for pressurizing the space 104 the pressure relief valve 144 is closed according to a representative embodiment. In another embodiment, the pressure relief valve 144 is at least partially open during pressurizing the medium 122 in the space 104. In such a configuration, the pump device 138 has to be operated at a suitable pump rate in order to maintain the pressure in the space 104 in a predetermined pressure range. If the return path 134 is fluidically connected to the reservoir 140, in such a configuration a circulation of the medium 122 through the space 104 can be obtained.

According to a representative embodiment, the injection device 200 comprises a controller 146 for controlling the operation of at least one of the pump device 138, and the pressure relief valve 144. It should be understood that in accordance with embodiments of the herein disclosed subject-matter, the supply path 130, the pump device 138 and, if present, the check valve 142 form a pressure source 132 in accordance with embodiments of the herein disclosed subject-matter.

According to a representative embodiment, the controller 146 is adapted for controlling the pressure source 132. In particular, according to a representative embodiment, the controller 146 is adapted for controlling the pump device 138. In particular, the controller 146 is adapted for controlling the pump device 138 so as to pressurize the medium 122 in the space 104. In accordance with a representative embodiment, the controller 146 is configured for receiving a control signal 148, the control signal 148 indicating that the flow path element 116 is received in the seat 110. In response to the control signal 148 the controller 146 provides a control signal 150 to the pressure source 132, e.g. to the pump device 138, in order to pressurize the medium 122 in the space. According to a representative embodiment, the injection device 200 comprises a sensor 152, e.g. a pressure sensor, which provides a control signal 154 to the controller, the control signal 154 being indicative of the pressure in the medium 122 in the space 104. In accordance with a representative embodiment, the injection device 200 comprises a control element 156, the control element 156 being activatable by an operator in order to provide the control signal 148 indicating that the flow path element 116 is received in the seat 110. Additionally or alternatively to the control element 156, for example additionally as described with regard to FIG. 2, the injection device 200 comprises an actuator 158 for coupling the flow path element 116 fluidically to the seat 110.

In accordance with a representative embodiment, the controller 146 provides a control signal 160 to the actuator 158 in order to operate the actuator 158 according to a predetermined operation program defined in the controller 146. In accordance with a representative embodiment, the actuator 158 provides a feedback signal 162 which is indicative of the position of the flow path element 116 with regard to the seat 110. According to a representative embodiment, the controller 146 is adapted for pressurizing the medium 122 in the space 104 if the feedback signal 162 indicates that the flow path element 116 is received in the seat 110. According to a further embodiment, the controller 146 is adapted for enabling pressurizing the medium 122 in the space 104 if the feedback signal 162 indicates that the flow path element 116 is received in the seat 110, whereas pressurizing the medium 122 is effected by the controller 146 in response to a further control signal, e.g. generated by a respective user input or by a operation program defined in the controller 146.

In accordance with a representative embodiment, the controller 146 is adapted for providing a control signal 164 to the pressure relief valve 144 in order to operate the pressure relief valve 144 in accordance with embodiments of the herein disclosed subject-matter. According to a representative embodiment, the controller 146 opens the pressure relief valve 144 by means of control signals 164 in accordance with a user input or in accordance with a predefined program defined in the controller 146. In accordance with a representative embodiment, the controller 146 provides a control signal 160 to the actuator 158 for effecting a withdrawal of the flow path element 116 out of the seat 110 only if the pressure relief valve 144 is open for a predetermined time and/or if the sensor signal 154 indicates that the pressure in the medium 122 in the space 104 is below a predetermined pressure, e.g. below the predetermined first pressure.

According to a representative embodiment, the controller 146 comprises or consists of a data processing system 166 or a processor device for executing at least one software module in order to have the controller 146 providing the functionality according to one or more embodiments of the herein disclosed subject matter.

Figure 3:
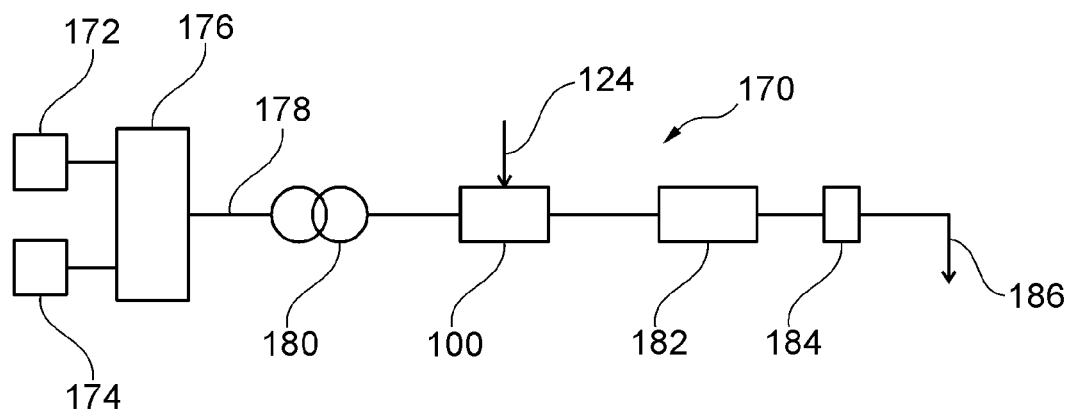
FIG. 3 shows a measuring device in accordance with embodiments of the herein disclosed subject-matter.

FIG. 3 shows a measuring device 170 in accordance with embodiments of the herein disclosed subject-matter.

In accordance with a representative embodiment, the measuring device 170 comprises an injection device in accordance with embodiments of the herein disclosed subject-matter, such as the injection device 100 shown in FIG. 1. Further, the measuring device 170 comprises two reservoirs 172, 174 which are fluidically coupled to a proportioning valve 176, wherein the proportioning valve 176 provides a mobile phase 178 containing at least one of the liquids of the two reservoirs 172, 174 to a fluid drive unit 180. In accordance with a representative embodiment, the measuring device 170 comprises the fluid drive unit 180, such as a pump, in order to drive the mobile phase 178 through the injection device 100, where a pressurized fluid 124 in the form of a fluidic sample is injected into the mobile phase 178. Having again regard to FIG. 2, it should be understood that according to a representative embodiment the mobile phase 178 may be provided in the flow path 136 of the FIG. 2.

In accordance with a representative embodiment, the measuring device 170 comprises a separation unit 182, such as a chromatographic column. In accordance with a representative embodiment, the separation unit 182 is configured for separating compounds of the fluidic sample in the mobile phase 178. Further in accordance with a representative embodiment, the measuring device 170 comprises a detector 184 for detecting the separated compounds of the sample fluid in the mobile phase 178. Downstream of the detector 184, the mobile phase 178 and the sample fluid may be provided to a waste, indicated at 186 in FIG. 3.

It should be noted that any entity disclosed herein, (e.g. a component, element, unit, software module and device) is not limited to a dedicated entity as described in some embodiments. Rather, the herein disclosed subject-matter may be implemented in various ways and with various granularity on device level and on software module level while still providing the desired functionality. Further, it should be noted that according to embodiments a separate entity (e.g. a component, element, unit, software module and device) may be provided for each of the functions disclosed herein. According to other embodiments, an entity is configured for providing two or more functions as disclosed herein. According to a representative embodiment, the controller 146 comprises a processor device including at least one processor for carrying out at least one computer program corresponding to a respective software module.

In this regard it should be mentioned that according to embodiments of the herein disclosed subject-matter, any function of the controller 146 may be provided in the form of a respective computer program module which enables a processor device to provide the respective function. According to other embodiments, any function of the controller 146 may be provided in hardware. According to other-hybrid-embodiments, some functions are provided in software while other functions are provided in hardware. It should be understood that the controller 146 accordingly may include different numbers of software modules and/or hardware modules for performing the function as disclosed with regard to embodiments of the herein disclosed subject-matter. According to a representative embodiment, the processor device is a data processing system.

It should be noted that any embodiment disclosed herein may be combined with one or more other embodiments disclosed herein unless otherwise noted or unless technically infeasible.

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. An injection device, comprising:
    a housing defining a space;
    a seat located in said space, the seat being configured for receiving a flow path element at a flow path connection site in the space, wherein the flow path element is configured for injecting a pressurized fluid through the seat; and
    a pressure source for pressurizing a medium surrounding the flow path connection site in said space, thereby reducing the pressure difference between the pressurized fluid in said flow path element and said medium.

2. The injection device according to claim 1, further comprising at least one of the following features:
    the pressure source comprises a pump device and a supply path, the pump device being configured for providing said medium under pressure through said supply path;
    the pressure source comprises a supply path for flow of said medium into the space and a return path for flow of said medium out of the space, wherein the supply path and the return path are provided by the same flow path;
    the pressure source comprises a supply path for flow of said medium into the space and a return path for flow of said medium out of the space, wherein the supply path is different from the return path.

3. The injection device according to claim 1, wherein:
    the housing comprises a base and a cover, and the seat is located in the base; and
    the cover is mounted or mountable on the base, the cover and the base thereby defining the space.

4. The injection device according to claim 3, further comprising at least one of the following features:

the cover is configured for being penetratable by said flow path element;

the cover comprises a housing body, the housing body comprising a through-hole facing said seat;

the cover comprises a housing body, the housing body comprising a through-hole facing said seat, the through hole being covered by a pressure seal which is penetratable by said flow path element.

5. The injection device according to claim 1, wherein the medium is selected from the group consisting of:

the medium is a fluid;

the medium is a gel;

the medium comprises a fluid;

the medium comprises a gel;

the medium has a viscosity in a range between 0.0001 Pas and 300 Pas;

the medium has a viscosity in a range between 0.0001 Pas and 0.01 Pas;

the medium has a viscosity in a range between 0.01 Pas and 1.0 Pas; and the medium has a viscosity in a range between 1.0 Pas and 200 Pas.

6. The injection device according to claim 1, wherein the flow path element is an injection needle.

7. The injection device according to claim 1, wherein the pressurized fluid is selected from the group consisting of:

the pressurized fluid is a liquid;

the pressurized fluid is a gas;

the pressure of the pressurized fluid is above 100 bar;

the pressure of the pressurized fluid is above 300 bar;

the pressure of the pressurized fluid is above 500 bar; and the pressure of the pressurized fluid is above 1000 bar.

8. The injection device according to claim 1, further comprising a controller for controlling the pressure source.

9. The injection device according to claim 8, wherein the controller is configured for reducing the pressure of the medium in the space before said flow path element is removed from said seat.

10. A measuring device for performing a measurement on a fluidic sample, the measuring device comprising:

an injection device according to claim 1.

11. A measuring device according to claim 10, wherein the fluidic sample is a mobile phase and the measuring device is a fluid separation system for separating compounds of a sample fluid in the mobile phase, and the fluid separation system comprises a feature selected from the group consisting of:

the injection device is provided for injection of the sample fluid into the mobile phase;

the fluid separation system comprises a mobile phase drive configured to drive the mobile phase through the fluid separation system;

the fluid separation system comprises a separation unit configured for separating compounds of the sample fluid in the mobile phase; and a combination of two or more of the foregoing.

12. A method of sealing a flow path connection site in an injection device wherein a flow path element carries a pressurized fluid, the method comprising:

receiving the flow path element in a seat of the flow path connection site such that the flow path element is configured for injecting the pressurized fluid through the seat; and pressurizing a medium which surrounds the flow path connection site to thereby reduce the pressure difference between the pressurized fluid in said flow path element and said medium.

13. The method according to claim 12, further comprising a feature selected from the group consisting of:

pressurizing the medium comprises supplying said medium under pressure into a space, which surrounds the flow path connection site;

receiving a control signal indicating that said flow path element is received in said seat and, in response hereto, providing a control signal in order to pressurize said medium;

maintaining the pressure of the medium in a predetermined range;

receiving a sensor signal, which is indicative of the pressure in said medium and controlling a pressure source in response to said sensor signal to thereby pressurize said medium;

receiving a control signal from a control element that is activatable by an operator, the control signal indicating said flow path element is received in said seat and, in response hereto, pressurizing said medium;

receiving a sensor signal indicating that said flow path element is received in said seat and, in response hereto, pressurizing said medium;

determining from the operation of an actuator that said flow path element is received in said seat, and, in response hereto, pressurizing said medium; and a combination of two or more of the foregoing.

14. The method according to claim 12, further comprising determining whether said flow path element is to be removed from said seat and, in response hereto, reducing the pressure in said medium.

15. A tangible non-transitory computer-readable medium executable by a computer processor or other processing device software program or product, for controlling or executing a method of claim 12, when run on a data processing system.

16. The injection device according to claim 8, comprising a feature selected from the group consisting of:

the controller is configured so as to pressurize the medium if said flow path element is received in said seat;

the controller is configured for receiving a control signal indicating that said flow path element is received in said seat, wherein the controller, in response hereto, provides a control signal to said pressure source in order to pressurize said medium;

the controller is configured for maintaining the pressure of the medium in the space in a predetermined range;

the injection device comprises a sensor providing a sensor signal which is indicative of the pressure in said medium, the controller controlling the pressure source in response to said sensor signal;

the injection device comprises a control element activatable by an operator in order to signal to the controller that said flow path element is received in said seat;

the injection device comprises a sensor for determining that said flow path element is received in said seat;

the injection device comprises an actuator for coupling said flow path element and said seat, the controller determining from the operation of the actuator whether said flow path element is received in said seat;

the injection device comprises an actuator for coupling said flow path element and said seat, the controller determining from the operation of the actuator whether said flow path element is received in said seat, wherein the controller receives a feedback signal from the actuator;

the injection device comprises an actuator for coupling said flow path element and said seat, the controller determining from the operation of the actuator whether said flow path element is received in said seat, wherein the controller is configured for controlling the actuator; and a combination of two or more of the foregoing.

17. The injection device according to claim 9, wherein the controller has a configuration selected from the group consisting of:

the controller is configured for providing a control signal to the pressure source, the control signal effecting the reduction of the pressure of the medium in the space;

the controller is configured for operating a pressure relief valve in a return path to thereby open the return path to allow said medium to flow out of the space; and both of the foregoing.

18. The method according to claim 14, comprising a step selected from the group consisting of:

effecting reduction of the pressure of the medium by providing a control signal to a pressure source;

effecting reduction of the pressure of the medium by opening a return path to allow said medium to flow out of the space; and both of the foregoing.

19. The method according to claim 1, wherein the pressure source comprises a supply path configured for allowing flow of the medium into the space.

20. The method according to claim 1, wherein the housing is configured for allowing removable insertion of the flow path element into the space.

\* \* \* \* \*